United States Patent
Ochiai et al.

(10) Patent No.: US 7,429,588 B2
(45) Date of Patent: Sep. 30, 2008

(54) CRYSTALLINE ISOXAZOLE DERIVATIVE AND MEDICAL PREPARATION THEREOF

(75) Inventors: Yasushi Ochiai, Suita (JP); Kazuhiko Tomomura, Ibaraki (JP); Hiroyuki Nishii, Takatsuki (JP)

(73) Assignee: Dainippon Sumitomo Pharma Co., Ltd., Osaka-shi (JP)

( * ) Notice: Subject to any disclaimer, the term of this patent is extended or adjusted under 35 U.S.C. 154(b) by 100 days.

(21) Appl. No.: 10/473,005

(22) PCT Filed: Mar. 26, 2002

(86) PCT No.: PCT/JP02/02937

§ 371 (c)(1), (2), (4) Date: Sep. 26, 2003

(87) PCT Pub. No.: WO02/092094

PCT Pub. Date: Nov. 21, 2002

(65) Prior Publication Data

US 2004/0082580 A1    Apr. 29, 2004

(30) Foreign Application Priority Data

Mar. 27, 2001    (JP) .............................. 2001-089119

(51) Int. Cl.
*A61K 31/5377*    (2006.01)
*C07D 413/12*    (2006.01)

(52) U.S. Cl. .................... 514/236.8; 544/137

(58) Field of Classification Search ................. 544/137; 514/236.8
See application file for complete search history.

(56) References Cited

U.S. PATENT DOCUMENTS 6,100,260 A    8/2000    Nakatsuka et al.

2005/0158371 A1*    7/2005    Nishikado et al. ........... 424/449

FOREIGN PATENT DOCUMENTS

| EP | 1 138 674 A1 | 10/2001 |
| JP | 2000-186038 A | 7/2000 |
| JP | 2000-186077 A | 7/2000 |
| WO | WO 98/47880 A1 | 10/1998 |
| WO | WO 00/29383 A1 | 5/2000 |

OTHER PUBLICATIONS

Brittain polymorphism in pharmaceutical solids Marcel Dekker, p. 1, 2, 178-179, 185, 219 and 236 (1000).*
US Pharmacopia #23, national formulary #18, p. 1843-1844, 1995.*
A. Maureen Rouhi, Chemical & Engineering News, Feb. 24, 2003, pp. 32-35.*
(http://www.ninds.nih.gov/health_and_medical/disorders/aids.htm). accessed May 31, 2004.*
Byrn et al. "Solid-State Chemistry of Drugs" (1999), pp. 62-63.*
Edited by Sadasuke Okano, Shin•Yakuzaigaku Soron (3rd revised edition), Kabushiki Kaisha Nankodo, 1987nen, pp. 138, 255, 256.

* cited by examiner

*Primary Examiner*—Rebecca L Anderson
(74) *Attorney, Agent, or Firm*—Sughrue Mion, PLLC

(57) ABSTRACT

Crystalline 3-[(1S)-1-(2-fluorobiphenyl-4-yl)ethyl]-5-{[amino(morpholin-4-yl)methylene]amino}-isoxazole that exhibits the following angle of diffraction (2θ) and relative intensity in a powder X-ray diffraction pattern, is very easy to handle and stable in a process of its formulation into a pharmaceutical preparation.

| 2θ (°) | Relative intensity (%) |
|---|---|
| 6.1 | 100 |
| 14.1 | 55 |
| 16.0 | 74 |
| 18.5 | 36 |
| 20.0 | 43 |
| 25.4 | 39 |

2 Claims, No Drawings

CRYSTALLINE ISOXAZOLE DERIVATIVE AND MEDICAL PREPARATION THEREOF

This application is a 371 of PCT/JP02/02937 filed Mar. 26, 2002.

TECHNICAL FIELD

The present invention relates to a crystal-line isoxazole derivative useful as a therapeutic agent for autoimmune diseases, inflammatory diseases and the like, and a pharmaceutical preparation containing said derivative.

BACKGROUND ART

WO 98/47880 and JP-A-2000-186077 disclose that 3-[(1S)-1-(2-fluorobiphenyl-4-yl)ethyl]-5-{[amino(morpholin-4-yl)methylene]amino}isoxazole represented by the following formula 1 is useful as, for example, an excellent therapeutic agent for autoimmune diseases, inflammatory diseases and the like:

Formula 1:

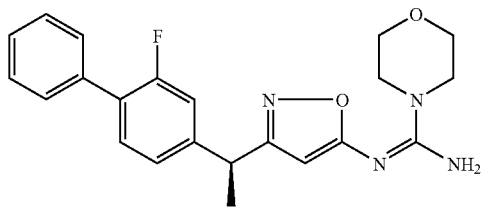

However, although these references disclose the isoxazole derivative of the formula 1, they do not disclose crystalline isoxazole derivative of the formula 1 which is easy to handle and stable in a process of its formulation into a pharmaceutical preparation and a pharmaceutical preparation containing this derivative.

Iyakushin (Pharmaceutical Council) No. 64 (issued on Feb. 14, 2000) supplies "guidelines for a bioequivalence test on oral solid pharmaceutical preparations different in the content of an active ingredient", and it has become necessary that oral solid pharmaceutical preparations different in the content of an active ingredient should exhibit equivalent release-by-dissolution behaviors in each of test solutions (e.g. buffer solutions or water) having pH values of 1.2, 3.0 to 5.0 and 6.8, respectively, corresponding to the pH values in digestive tracts. Pharmaceutical preparations having good release-by-dissolution properties are relatively easy to obtain as pharmaceutical preparations that exhibit equivalent release-by-dissolution behaviors irrespective of their different active ingredient contents, but the production of a pharmaceutical preparation of a difficultly water-soluble compound such as the isoxazole derivative of the formula 1 is generally difficult because the compound has a low affinity for water.

DISCLOSURE OF THE INVENTION

The present inventors earnestly investigated the formulation of the isoxazole derivative of the formula 1 into a pharmaceutical preparation. Consequently, the present inventors found that as the isoxazole derivative of the formula 1, at least two crystal types (referred to as α type crystals and β type crystals) exist. Since the isoxazole derivative of the formula 1 is difficultly water-soluble, its crystals are preferably finely ground in its formulation into a pharmaceutical preparation. Therefore, the crystals of the two types were subjected to pneumatic grinding and wet grinding, i.e., grinding of the crystals suspended in water. The results of the tests carried out in Test Examples 1 to 4 are summarized below.

(1) Grinding of the α Type Crystals

When the α type crystals were subjected to pneumatic grinding, they adhered remarkably to the inside of a grinding apparatus. Therefore, their pulverization to a desirable size by one run of grinding operation was difficult, so that it was necessary to grind them repeatedly several times. Since it often became necessary to remove the crystals adhering to the inside, the grinding efficiency and the yield were low. When a wet grinding method was adopted, the α type crystals became very bulky and hence were difficult to disperse in a dispersion medium such as water, so that they could not be formulated to a pharmaceutical preparation. In the case of wet grinding under high-pressure grinding conditions, the α type crystals changed to the β type crystals during the treatment of the α type crystals suspended in water.

(2) Grinding of the β Type Crystals

When the β type crystals were subjected to pneumatic grinding, they hardly adhered to the inside of a grinding apparatus, were easy to handle in a process of their formulation into a pharmaceutical preparation, and could be continuously ground. The β type crystals could easily be ground also by a wet grinding method and made it possible to produce finer powder that could be formulated into a pharmaceutical preparation. In addition, these grindings did not change the crystal type.

From the above test results, it was found that the crystalline isoxazole derivative of the formula 1 of the present invention as the β type crystals is very easy to handle and stable in a process of its formulation into a pharmaceutical preparation.

Furthermore, the present inventors found that an oral pharmaceutical preparation containing a water-soluble excipient in an amount of 2.5 times or more the weight of the isoxazole derivative of the formula 1 has good release-by-dissolution properties.

On the basis of the above findings, the present inventors have accomplished the present invention. The present invention is as follows.

[1] Crystalline 3-[(1S)-1-(2-fluorobiphenyl-4-yl)ethyl]-5-{[amino(morpholin-4-yl)methylene]amino}-isoxazole that exhibits the following angle of diffraction (2θ) and relative intensity in a powder X-ray diffraction pattern:

TABLE 1

| 2θ (°) | Relative intensity (%) |
| --- | --- |
| 6.1 | 100 |
| 14.1 | 55 |
| 16.0 | 74 |
| 18.5 | 36 |
| 20.0 | 43 |
| 25.4 | 39 |

[2] Crystalline 3-[(1S)-1-(2-fluorobiphenyl-4-yl)ethyl]-5-{[amino(morpholin-4-yl)methylene]amino}-isoxazole according to [1], which is in a grounded state and has an undersize particle D50% particle size of 10 μm or less.

[3] A pharmaceutical preparation comprising crystalline 3-[(1S)-1-(2-fluorobiphenyl-4-yl)ethyl]-5-{[amino(morpholin-4-yl)methylene]amino}isoxazole according to [1] or [2].

[4] A pharmaceutical preparation according to [3], which is a therapeutic or prophylactic agent for autoimmune diseases or inflammatory diseases.

[5] A process for producing crystalline 3-[(1S)-1-(2-fluorobiphenyl-4-yl)ethyl]-5-{[amino(morpholin-4-yl)methylene]amino}isoxazole by crystallizing 3-[(1S)-1-(2-fluorobiphenyl-4-yl)ethyl]-5-{[amino(morpholin-4-yl)methylene]amino}isoxazole from a mixed solvent of a hydrophilic solvent and water.

[6] A production process according to [5], wherein the hydrophilic organic solvent is 2-propanol, methanol or acetone.

[7] An oral pharmaceutical preparation comprising crystalline 3-[(1S)-1-(2-fluorobiphenyl-4-yl)ethyl]-5-{[amino(morpholin-4-yl)methylene]amino}isoxazole according to [1] or [2], a water-soluble excipient in an amount of 2.5 times or more the weight of the crystalline isoxazole derivative, a disintegrating agent and a water-soluble binder.

[8] An oral pharmaceutical preparation according to [7], wherein the contents of the ingredients are the following percentages by weight:
the crystalline 3-[(1S)-1-(2-fluorobiphenyl -4-yl)ethyl]-5-{[amino(morpholin-4-yl)methylene]amino}-isoxazole: 25% or less,
the water-soluble excipient: 35 to 90%,
the disintegrating agent: 1 to 40%,
the water-soluble binder: 1 to 5%.

[9] An oral pharmaceutical preparation according to [7] or [8], wherein the water-soluble excipient is lactose, mannitol, erythritol, xylitol, or a mixture thereof.

[10] An oral pharmaceutical preparation according to any one of [7] to [9], wherein the disintegrating agent is sodium croscarmelose, sodium carboxymethyl starch, crospovidone, calcium carmelose, low-substituted hydroxypropyl cellulose, starch, or a mixture thereof.

[11] An oral pharmaceutical preparation according to any one of [7] to [10], wherein the water-soluble binder is hydroxypropylmethyl cellulose, hydroxypropyl cellulose, polyvinylpyrrolidone, polyvinyl alcohol, pullulan, or a mixture thereof.

[12] An oral pharmaceutical preparation according to any one of [7] to [11], which is tablets.

[13] A pharmaceutical preparation according to any one of [7] to [12], which is a therapeutic or prophylactic agent for autoimmune diseases or inflammatory diseases.

[14] A process for producing an oral pharmaceutical preparation according to any one of [7] to [13] by the following steps:
(1) mixing the water-soluble excipient and the disintegrating agent to prepare a mixture,
(2) dispersing crystalline 3-[(1S)-1-(2-fluorobiphenyl-4-yl)ethyl]-5-{[amino(morpholin-4-yl)methylene]amino}isoxazole according to [1] or [2] in an aqueous solution of the water-soluble binder to prepare a suspension,
(3) spraying the suspension of (2) on the mixture of (1) to prepare granules, and
(4) compression-molding the granules of (3).

[15] A process for producing an oral pharmaceutical preparation according to any one of [7] to [13] by the following steps:
(1) mixing crystalline 3-[(1S)-1-(2-fluorobiphenyl-4-yl) ethyl]-5-{[amino(morpholin-4-yl)methylene]amino}isoxazole according to [1] or [2], the water-soluble excipient and the disintegrating agent to prepare a mixture,
(2) preparing an aqueous solution of the water-soluble binder,
(3) spraying the aqueous solution of (2) on the mixture of (1) to prepare granules, and
(4) compression-molding the granules of (3).

The crystalline isoxazole derivative (β type crystals) of the formula 1 of the present invention may be produced, for example, by crystallizing the noncrystalline isoxazole derivative of the formula 1 from a mixed solvent of a hydrophilic solvent and water. The noncrystalline isoxazole derivative of the formula 1 may be produced, for example, by either of the processes disclosed in WO 98/47880 and JP-A-2000-186077. The hydrophilic solvent includes, for example, alcohols (e.g. 2-propanol, ethanol, methanol and t-butanol), ketones (e.g. acetone and 2-butanone), nitrites (e.g. acetonitrile and propionitrile), amides (e.g. N,N-dimethylformamide), and mixed solvents thereof, preferably alcohols such as 2-propanol, ethanol and methanol and ketones such as acetone, in particular, 2-propanol. The hydrophilic solvent may be incorporated with a small amount of any of aromatic hydrocarbons (e.g. toluene, chlorobenzene and benzene), ethers (e.g. t-butyl methyl ether, diisoproyl ether and diethyl ether), aliphatic hydrocarbons (e.g. cyclohexane, hexane and heptane), halogen-containing solvents (e.g. chloroform, methylene chloride and 1,2-dichloroethane) and esters (e.g. ethyl acetate).

Although the amount of the mixed solvent of the hydrophilic solvent and water is varied depending on the kind of the hydrophilic solvent used, it is usually, for example, in the range of about 5 to about 100 times, preferably about 10 to about 50 times, the weight of the noncrystalline isoxazole derivative of the formula 1 from the viewpoint of handling of the mixed solvent. Although the weight ratio of the hydrophilic solvent to water is varied depending on the kind of the hydrophilic solvent used, it is, for example, about 100:0 to about 1:10, preferably about 1:1 to about 1:5. In the crystallization, seed crystals for the β type crystals are preferably added. The crystallization temperature is, for example, in the range of about 70 to about 0° C. The noncrystalline isoxazole derivative of the formula 1 is preferably dissolved at about 70 to about 40° C. at first, cooled slowly and stepwise or continuously, and crystallized at about 20 to about 0° C. In addition, it is preferable to dissolve the noncrystalline isoxazole derivative of the formula 1 in the hydrophilic solvent and then add water thereto to crystallize this derivative.

For obtaining the crystalline isoxazole derivative of the formula 1 having a high purity, the following is preferable: after crystals of phosphate or the like of the isoxazole derivative are isolated, the phosphate or the like is made into the free isoxazole derivative and then the free isoxazole is crystallized. In this case, the salt of the isoxazole derivative of the formula 1 is made into the free isoxazole derivative and the free isoxazole derivative may be crystallized in the same reactor by replacing the solvent for reaction with a hydrophilic organic solvent when it is a hydrophobic organic solvent, or by using the solvent for reaction as it is when it is a hydrophilic organic solvent. A base used for making the salt into the free isoxazole derivative includes, for example, alkali hydroxides (e.g. sodium hydroxide and potassium hydroxide) and alkali carbonates (e.g. sodium carbonate, sodium hydrogencarbonate, potassium carbonate and potassium hydrogencarbonate). An aqueous solution of the base may be used.

The β type crystals of the present invention may be obtained also by stirring phosphate or α type crystals of the isoxazole derivative of the formula 1 in a suspended state in water for a definite time. In the case of the phosphate, the β type crystals could be obtained, for example, by stirring the phosphate at 50° C. for about 5 hours. Also from this fact, it can be seen that the β type crystals are thermodynamically more stable than the α type crystals. So long as seed crystals for the β type crystals are used, it is also possible to produce the β type crystals by using any of hydrophobic organic solvents such as aromatic hydrocarbons (e.g. toluene and benzene), ethers (e.g. t-butyl methyl ether, diisopropyl ether and diethyl ether), aliphatic hydrocarbons (e.g. cyclohexane, hexane and heptane), halogen-containing solvents (e.g. chloroform, methylene chloride and 1,2-dichloroethane) and esters (e.g. ethyl acetate). For example, the isoxazole derivative of the formula 1 may be crystallized by dissolving the derivative in a mixed solvent of toluene and 2-propanol and adding hexane thereto.

On the other hand, the α type crystals may be obtained by dissolving phosphate of the isoxazole derivative of the formula 1 in water and cooling the resulting solution rapidly.

When used as a therapeutic or prophylactic agent, the crystalline isoxazole derivative of the formula 1 of the present invention may be administered orally or parenterally (for example, by intravenous, subcutaneous or intramuscular injection, locally, intrarectally, percutaneously, or through nose). Forms for the oral administration includes, for example, tablets, capsules, pills, granules, powders, solutions, syrups and suspensions. Forms for the parenteral administration include, for example, aqueous or oily preparations for injection, ointments, creams, lotions, aerosols, suppositories and patches. These pharmaceutical preparations are prepared by conventional techniques and may contain carriers, excipients, binders, stabilizers and the like, which are acceptable and conventionally used. When the crystalline isoxazole derivative of the formula 1 is used in the form of an injection, a buffer, solubilizer tonicity agent and the like may be added which are acceptable.

Although the dose and the number of administrations of the crystalline isoxazole derivative of the formula 1 are varied depending on symptom, age, body weight and administration route, it may be administered to an adult (body weight: 50 kg) usually in a dose of approximately 5 to 200 mg, preferably 10 to 50 mg, (in terms of the compound of the present invention as an active ingredient) per day in one portion or several portions.

The crystalline isoxazole derivative of the formula 1 is useful as a therapeutic or prophylactic agent for diseases such as autoimmune diseases [e.g. rheumatoid arthritis, systemic lupus erythematosus, systemic scleroderma, Sjögren syndrome, Hashimoto disease, myasthenia gravia, Basedow disease, Addison disease, juvenile-onset diabetes (type I diabetes), autoimmune hematic diseases (e.g. aplastic anemia, hemolytic anemia and sudden thrombocytopenia), ulcerative colitis, active chronic hepatitis, glomerular nephritis, interstitial pneumosclerosis and disseminated sclerosis], and inflammatory diseases [e.g. arthritis deformans, gout, atopic dermatitis and psoriasis].

An oral pharmaceutical preparation comprising the crystalline isoxazole derivative of the formula 1 of the present invention, a water-soluble excipient in an amount of 2.5 times the weight of the derivative, a disintegrating agent and a water-soluble binder has good release-by-dissolution properties. A preferable form of the oral pharmaceutical preparation is, for example, tablets. Said oral pharmaceutical preparation exhibited a release-by-dissolution rate of 75% at 15 minutes in a test solution of pH 3.5 even when the content of the active ingredient is varied.

As preferable weight proportions of the above ingredients, there may be exemplified the following weight proportions based on the weight of the oral pharmaceutical preparation:

the crystalline isoxazole derivative of the formula 1: 25% or less,
the water-soluble excipient: 35 to 90%,
the disintegrating agent: 1 to 40%, and
the water-soluble binder: 1 to 5%.

The water-soluble excipient includes, for example, sugars such as lactose, sucrose, fructooligo-saccharide, paratinose, glucose, maltose, reducing maltose, maltose syrup powder, fructose, isomerized lactose, reducing lactose, honey sugar, etc.; sugar alcohols such as mannitol, erythritol, xylitol, maltitol, etc.; and mixtures thereof. Preferable examples of the water-soluble excipient are lactose, mannitol, erythritol, xylitol, and mixtures thereof.

The disintegrating agent includes, for example, sodium croscarmelose, sodium carboxymethyl starch, crospovidone, calcium carmelose, low-substituted hydroxypropyl cellulose, corn starch, crystalline cellulose, carmelose, sodium carmelose, anhydrous calcium hydrogenphosphate, calcium phosphate, magnesium aluminate metasilicate, synthetic hydrotalcite, synthetic aluminum silicate, and mixtures thereof. Preferable examples of the disintegrating agent are sodium croscarmelose, sodium carboxymethyl starch, crospovidone, calcium carmelose, low-substituted hydroxypropyl cellulose, natural starches (e.g. corn starch), and mixtures thereof.

The water-soluble binder includes, for example, hydroxypropylmethyl cellulose, hydroxypropyl cellulose, polyvinylpyrrolidone, polyvinyl alcohol, pullulan, starches, dextrins, gelatin, and mixtures thereof. Preferable examples of the water-soluble binder are hydroxypropylmethyl cellulose, hydroxypropyl cellulose, polyvinylpyrrolidone, polyvinyl alcohol, pullulan, and mixtures thereof.

The oral pharmaceutical preparation may be produced in the same manner as, for example, in the following production process 1 and production process 2. In the production, previous finely grinding of the crystalline isoxazole derivative of the formula 1 is preferable, and the undersize particle D50% particle size of the ground derivative is preferably, for example, about 10 μm or less, more preferably about 7 μm or less, and is, for example, in the range of about 1 to about 7 μm.

Production Process 1

(1) Preparation of an Aqueous Solution of a Water-soluble Binder

An aqueous solution of a water-soluble binder may be prepared by dissolving the binder in purified water. The temperature at the dissolution is, for example, in the range of about 20° C. to about 90° C., preferably about 20° C. to about 70° C. The amount of the purified water used is, for example, about 5 to about 50 times, preferably about 10 to about 30 times, the weight of the water-soluble binder.

(2) Preparation of an Aqueous Suspension of the Crystalline Isoxazole Derivative of the Formula 1

A suspension of the crystalline isoxazole derivative of the formula 1 may be prepared by dispersing the derivative in the water-soluble binder aqueous solution prepared in (1). The temperature at the dispersion is, for example, in the range of about 20° C. to about 90° C., preferably about 20° C. to about 40° C.

(3) Preparation of Granules

A water-soluble excipient, a disintegrating agent and optionally (when desired to be incorporated) starch are charged into a granulator and mixed. Then, the resulting mixture is granulated while being sprayed with the aqueous suspension prepared in (2). The air supply temperature at the granulation is, for example, in the range of about 50° C. to about 90° C., preferably about 60° C. to about 80° C. The granulation time is, for example, in the range of about 30 to about 180 minutes, preferably about 40 to about 150 minutes. A method for the granulation includes, for example, fluid bed granulation and roto granulation. A fluid bed granulator, a roto fluid bed granulator or the like may be used depending on the granulation method.

(4) Drying of the Granules

The granules prepared in (3) are dried under reduced pressure or at atmospheric pressure. This drying is preferably conducted so that the loss in weight on drying measured with an infrared moisture meter may be, for example, about 3 wt % or less, preferably about 2 wt % or less.

(5) Blending of a Lubricant

Although the dried granules obtained in (4) may be compressed into tablets as they are, they are preferably compressed into tablets after blending a lubricant therewith. The lubricant includes, for example, magnesium stearate, talc, hardened oil, stearic acid, calcium stearate, glycerol behenate, glycerol stearate and sodium stearyl fumarate. The amount of the lubricant blended is, for example, about 0.3 to about 3 wt %, preferably about 0.5 to about 1.5 wt %, based on the total weight of the tablets. The blending of the lubricant may be conducted by adding the lubricant to the dried granules obtained in (4), and mixing them. A mixing apparatus includes, for example, diffusion mixers [tumble]. Specifically, a tumble blender, V blender, double corn, bin tumbler and the like may be used.

(6) Tabletting

The mixture obtained in (5) is compressed into tablets by a conventional method. For example, a tablet press and the like may be used as a tabletting apparatus. The tabletting hardness is, for example, about 50 to about 200 N.

(7) Film Coating

If necessary, the tablets obtained in (6) may be coated with films, respectively. A coating material includes, for example, combinations of a base material (e.g. hydroxypropylmethyl cellulose, hydroxypropyl cellulose or polyvinylpyrrolidone) and a plasticizer (e.g. polyethylene glycol, propylene glycol, triacetin, triethyl citrate, glycerol or a glycerol fatty acid ester). In addition, if necessary, additives such as titanium oxide, mannitol and the like may be added. A coating apparatus includes, for example, a coating pan. A specific example thereof is a perforated coating system.

(8) Drying of the Tablets

The tablets coated in (7) are dried under reduced pressure or at atmospheric pressure. This drying is preferably conducted so that the loss in weight on drying measured with an infrared moisture meter may be, for example, about 3 wt % or less, preferably about 2 wt % or less.

Production Process 2

(1) Preparation of an Aqueous Solution of a Water-soluble Binder

An aqueous solution of a water-soluble binder is prepared in the same manner as in production process 1, (1).

(2) Preparation of Granules

The crystalline isoxazole derivative of the formula 1, a water-soluble excipient, a disintegrating agent and optionally (when desired to be incorporated) starch are charged into a granulator and mixed. Then, the resulting mixture is granulated while being sprayed with the aqueous solution prepared in (1). The granulation may be carried out by employing the same air supply temperature at granulation and granulation method as in production process 1, (3).

(3) Drying of the Granules, Blending of a Lubricant, Tabletting, Film Coating and Drying of Tablets Tablets may be produced in the same manner as in production process 1, (3) to (8).

EXAMPLES

The present invention is illustrated below in further detail with reference to examples, which should not be construed as limiting the scope of the invention.

Example 1

Production of the β Type Crystals

To 40.0 g of 2-propanol was added 4.0 g of the isoxazole derivative of the formula 1, and crystals of the isoxazole derivative were completely dissolved at 50° C. At the same temperature, 70 g of water was added thereto and stirred, followed by adding thereto seed crystals for the β type crystals. At the same temperature, 30 g of water was added dropwise thereto over a period of 25 minutes and stirred for another 35 minutes. The resulting mixture was slowly cooled to 25° C. over a period of 55 minutes and stirred at this temperature for 1 hour. The crystals precipitated were collected by filtration. The crystals obtained were washed with a 10% aqueous 2-propanol solution and then dried under reduced pressure to obtain 3.88 g (yield 97%) of the β type crystals of the isoxazole derivative of the formula 1 as needles.

Example 2

Production of the β Type Crystals

To 500 g of toluene and 187.5 g of 2-propanol was added 250 g of α type crystals of the isoxazole derivative of the formula 1, and the crystals were completely dissolved at 60° C. The resulting solution was filtered and the residue was washed with 62.5 g of 2-propanol. The filtrate and the washings were combined and 231 g of hexane was added dropwise to the combined solution at 50° C. Seed crystals for the β type crystals were added thereto, followed by adding dropwise thereto 2013 g of hexane, and the resulting mixture was stirred at the same temperature for 30 minutes, allowed to cool, and then stirred at 20 to 30° C. for 1 hour. The crystals precipitated were collected by filtration. The crystals obtained were washed with 1 L of hexane and then dried under reduced pressure to obtain 237.5 g (yield 95%) of the β type crystals of the isoxazole derivative of the formula 1 as needles.

Example 3

Production of the β Type Crystals

To 12.5 g (25.4 mmol) of phosphate of the isoxazole derivative of the formula 1 were added 56.3 g of water, 93.8 g of 2-propanol and 93.8 g of toluene, and the resulting mixture was heated at 30° C. to dissolve crystals of the phosphate completely. To the resulting solution was added dropwise 41.3 g (19.5 mmol) of a 5% aqueous sodium carbonate solution at the same temperature, and stirred for another 30 minutes, and the resulting solution was separated. To the organic layer was added 0.1 g of activated carbon, and the resulting mixture was stirred at 30° C. for 30 minutes. The activated carbon was filtered off and washed with 28.2 g of 2-propanol. The solution thus obtained was concentrated under reduced pressure to a total amount of 82.4 g, followed by adding thereto 282 g of 2-propanol, and the resulting mixture was concentrated under reduced pressure to a total amount of 75.5 g. To the resulting solution was added 34.5 g of 2-propanol (the amount of the residual toluene in the solution was measured by gas chromatography and found to be 0.22% based on the amount of 2-propanol). To the solution thus obtained were added 175 g of water and 1.3 g of toluene at 50° C., and the resulting mixture was cooled to 43° C. To this mixture were added 6 mg of seed crystals for the β type crystals, and 75 mg of water was added dropwise thereto to precipitate crystals. Further, the resulting mixture was maintained at 43° C. for 1 hour, cooled to 0° C. and then maintained at 0° C. for 1 hour, and the crystals thus precipitated were collected by filtration. The crystals obtained were washed with 60 g of a 10% aqueous 2-propanol solution and then dried under reduced pressure to obtain 9.8 g (24.9 mmol, yield 98%) of the β type crystals of the isoxazole derivative of the formula 1.

Reference Example 1

Production of the α Type Crystals

To 2.0 g (4.1 mmol) of phosphate of the isoxazole derivative of the formula 1 was added 40 g of water, and the resulting mixture was heated at 50° C. to dissolve the phosphate. The resulting solution was maintained at the same temperature for 1 minute and immediately cooled to 30° C., and the crystals were collected by filtration. The crystals obtained were dried under reduced pressure to obtain 1.22 g (3.1 mmol, yield 76%) of α type crystals of the isoxazole derivative of the formula 1 as leaflets.

Example 4

Powder X-ray Diffraction of the β Type Crystals and the α Type Crystals

Powder X-ray diffraction patterns were measured by the use of Cu.Kα with an X-ray diffraction apparatus RINT2500V (mfd. by RIGAKU CORPORATION). The values of angle of diffraction (2θ) in the powder X-ray diffraction have a standard accuracy of about ±0.1. The angle of diffraction (2θ) and relative intensity in the powder X-ray diffraction of the β type crystals of Example 1 are as shown in Table 1 exhibited above. The angle of diffraction (2θ) and relative intensity in the powder X-ray diffraction of the α type crystals of Reference Example 1 are as shown in Table 2.

TABLE 2

| 2θ (°) | Relative intensity (%) |
|---|---|
| 5.8 | 35 |
| 11.8 | 100 |
| 20.3 | 38 |
| 20.6 | 44 |
| 22.7 | 70 |
| 23.8 | 52 |
| 27.4 | 43 |

Test Example 1

Dry Pneumatic Grinding Method of Crystals-1

Crystals were charged into an A-O Jet Mill (mfd. by Seishin Enterprise Co., Ltd.) and subjected to pneumatic grinding at a forcing pressure of 0.49 MPa and a grinding pressure of 0.49 MPa. Table 3 shows the amounts of the α type and β type crystals, respectively, adhering to the inside of the apparatus in the case where 7 g each of the α type crystals and the β type crystals were manually charged at a charge rate of approximately 10 to 20 g/hour. It has already been confirmed that the charge rate does not remarkably affects the adhering amounts.

TABLE 3

| Crystals | Adhering amount |
|---|---|
| α type crystals | 2.06 g |
| β type crystals | 0.00 g |

It can be seen from the above results that the β type crystals hardly adhere to the inside of the apparatus during the pneumatic grinding, though a considerable amount of the α type crystals adhere to the inside of the apparatus during the pneumatic grinding.

Test Example 2

Dry Pneumatic Grinding Method of Crystals-2

Crystals were charged into a Jet O Mill Model JOM0101 (mfd. by Seishin Enterprise Co., Ltd.) and subjected to pneumatic grinding at a forcing pressure and a grinding pressure (which had been set at the same pressure) of 0.44 MPa to 0.49 MPa. Table 4 shows the particle size distribution of the ground crystals in the case where each of the α type crystals and the β type crystals were manually charged at a charge rate of approximately 1 to 2 kg/hour. A laser diffraction particle size distribution meter (dry measurement) was used for measuring the particle size distribution. It has already been confirmed that repeated grinding or the increase of the grinding pressure is necessary for further particle size reduction.

TABLE 4

| | α type crystals | β type crystals |
|---|---|---|
| Treating amount | 950 g | 900 g |
| Undersize particle D50% particle size | 27.6 μm | 4.7 μm |
| Undersize particle D50% particle size | 79.3 μm | 10.2 μm |

The following can be seen from the above results: by one run of the grinding operation, the α type crystals cannot be ground to a particle size that permits formulation of the α type crystals into a pharmaceutical preparation, but the β type crystals can be made into a ground product having a very small particle size as compared with the α type crystals, namely, the β type crystals can be ground to a particle size suitable for formulation of the β type crystals into a pharmaceutical preparation.

Test Example 3

Dry Pneumatic Grinding Method of Crystals-3

The number of grinding operations and an operating time required for grinding the α type crystals to a particle size that permits formulation of the α type crystals into a pharmaceutical preparation were investigated. Crystals were charged into a Jet O Mill and subjected to pneumatic grinding. Table 5 shows the recovery of the ground crystals and an operating time in the case where starting crystals were manually charged at a charge rate of approximately 1 to 2 kg/hour. It has already been confirmed that the grinding pressure does not remarkably affects the adhering amounts of the starting crystals.

When the α type crystals were repeatedly ground until their particle size became equal to that of a ground product of the β type crystals, six repetitions of the grinding were necessary.

TABLE 5

|  | α type crystals | β type crystals |
|---|---|---|
| Grinding pressure | 0.80 MPa | 0.44 MPa |
| Repeated grinding | Six repetitions | None (only one run) |
| Treating amount | 10 kg | 9 kg |
| Recovery | 82% | 99% |
| Operating time | 70 hours | 10 hours |

In the case of the β type crystals, the ground product could be obtained by the above pneumatic grinding at a lower grinding pressure without repeating the grinding. As a result, its recovery was higher than the recovery of the ground product of the α type crystals. Furthermore, the operating time could be greatly reduced. Thus, the efficiency of grinding of the β type crystals is very high.

Test Example 4

Wet High-pressure Grinding Method of Crystals

Crystals were charged into Microfluidizer Model M110Y (mfd. by Mizuho Industrial Co., Ltd.) together with water and subjected to high-pressure grinding. Table 6 shows the particle size distribution of the ground crystals. In this case, the α type crystals were solidified during the grinding. The solidified α type crystals had a water content of about 80% and was that formed by complete incorporation of water used for suspending the α type crystals. The particle size distribution was measured by dispersing the ground crystals in water in an agate mortar. A laser diffraction particle size distribution meter (wet measurement) was used for measuring the particle size distribution.

TABLE 6

|  | α type crystals | β type crystals |
|---|---|---|
| Grinding pressure | 100 MPa | 100 MPa |
| Treating amount (starting crystals/water) | 40 g/150 g | 20 g/75 g |
| Treatment time | 6 minutes (solidification) | 7 minutes |
| Undersize particle D50% particle size | 26.1 μm | 1.7 μm |
| Undersize particle D50% particle size | 58.1 μm | 3.2 μm |

The following was found: as described above, the α type crystals give only a ground product unsuitable for formulation of the α crystals into a pharmaceutical preparation because of their aggregation and solidification, while the β type crystals can be ground by wet grinding to a particle size that makes it possible to transfer the ground product as it is to a subsequent step in the formulation of the β type crystals into a pharmaceutical preparation or to dry the ground product.

Formulation Example 1

Tablets (20-mg Tablets)

Tablets (20-mg tablets) were produced by charging mannitol, corn starch and sodium croscarmelose into a fluid bed granulator according to the following recipe, granulating them while spraying them with a binding liquid obtained by dispersing and suspending the difficultly water-soluble active ingredient in a water-soluble polymer binder solution, blending the resulting granules with magnesium stearate, and then compressing the resulting mixture into tablets.

| Ingredient | Content (mg) |
|---|---|
| Isoxazole derivative (β type crystals) of formula 1 | 20 |
| Mannitol | 66 |
| Corn starch | 28 |
| Sodium croscarmelose | 6 |
| Hydroxypropylmethyl cellulose | 4 |
| Magnesium stearate | 1 |
| Total | 125 mg |

Formulation Example 2

Tablets (40-mg Tablets)

Tablets (40-mg tablets) were produced by charging mannitol, corn starch and sodium croscarmelose into a fluid bed granulator according to the following recipe, granulating them while spraying them with a binding liquid obtained by dispersing and suspending the difficultly water-soluble active ingredient in a water-soluble polymer binder solution, blending the resulting granules with magnesium stearate, and then compressing the resulting mixture into tablets.

| Ingredient | Content (mg) |
|---|---|
| Isoxazole derivative (β type crystals) of formula 1 | 40 |
| Mannitol | 132 |
| Corn starch | 56 |
| Sodium croscarmelose | 12 |
| Hydroxypropylmethyl cellulose | 8 |
| Magnesium stearate | 2 |
| Total | 250 mg |

Formulation Example 3

Film-coated Tablets

Film-coated tablets (20-mg tablets) having the following preparation were obtained by charging the uncoated tablets prepared in Formulation Example 1 into High-coater HCT30N (Freund Sangyo K.K.), and coating them so that the amount of each coating film might be 3 mg.

| Ingredient | Content (mg) |
|---|---|
| Uncoated tablets prepared in Formulation Example 1 | 125 |

-continued

| Ingredient | Content (mg) |
| --- | --- |
| Hydroxypropylmethyl cellulose | 2.13 |
| Macrogole 400 | 0.21 |
| Titanium oxide | 0.66 |
| Carnauba wax | Slight amount |
| Total | 128 mg |

Comparative Formulation Example

Tablets (Uncoated Tablets) Containing a Water-soluble Excipient in an Amount of Less than 2.5 Times the Weight of the Difficultly Water-soluble Drug Tablets (40-mg tablets) were produced by charging mannitol, corn starch and sodium croscarmelose into a fluid bed granulator according to the following recipe, granulating them while spraying them with a binding liquid obtained by dispersing and suspending the difficultly water-soluble active ingredient in a water-soluble polymer binder solution, blending the resulting granules with magnesium stearate and then compressing the resulting mixture into tablets.

| Ingredient | Content (mg) |
| --- | --- |
| Isoxazole derivative (β type crystals) of formula 1 | 40 |
| Mannitol | 52 |
| Corn starch | 22 |
| Sodium croscarmelose | 6 |
| Hydroxypropylmethyl cellulose | 4 |
| Magnesium stearate | 1 |
| Total | 125 mg |

Test Example 5

Dissolution Test

A dissolution test on the tablets prepared in Formulation Examples 1 to 3 and Comparative Formulation Example was carried out under the following conditions according to Japanese Pharmacopoeia, Dissolution Test No. 2:

test solution: diluted McILvaine buffer (pH 3.5), number of revolution of a paddle: 50 rpm, test solution: 900 ml.

The results of the dissolution test obtained for each tablet are shown below in terms of release-by-dissolution rate (%).

TABLE 7

| Tablets | 0 min. | 4 min. | 8 min. | 15 min. | 30 min. | 45 min. |
| --- | --- | --- | --- | --- | --- | --- |
| Formulation Example 1 | 0 | 15 | 53 | 86 | 98 | 98 |
| Formulation Example 2 | 0 | 20 | 51 | 78 | 92 | 96 |
| Formulation Example 3 | 0 | 18 | 53 | 86 | 100 | 100 |
| Comparative Formulation Example | 0 | 11 | 33 | 65 | 83 | 88 |

The tablets (20-mg tablets) of Formulation Example 1 exhibited such very good release-by-dissolution properties that the release-by-dissolution rate was 85% or more at 15 minutes.

In the case of the tablets (40-mg tablets) of Formulation Example 2 prepared so as to contain the active ingredient in an amount of twice that employed in Formulation Example 1, the release-by-dissolution rate at 15 minutes was 78%. This release-by-dissolution rate at 15 minutes is in the range of that of the tablets of Formulation Example 1±10%, namely, it has become apparent that the tablets of Formulation Example 2 exhibits a release-by-dissolution behavior equivalent to that of the tablets of Formulation Example 1.

In the case of the film-coated tablets of Formulation Example 3 obtained by coating the tablets of Formulation Example 1 with films, respectively, the release-by-dissolution rate after 15 minutes was 86% that was same as in the case of the tablets of Formulation Example 1. From this fact, it is conjectured that the film coating does not change the release-by-dissolution rate.

In the case of the tablets of Comparative Formulation Example obtained by blending a water-soluble excipient in an amount of less than 2.5 times the amount of the difficultly water-soluble drug, the release-by-dissolution rate after 15 minutes was 65%. Therefore, it is conjectured that this pharmaceutical preparation is clearly inferior in release-by-dissolution properties to the pharmaceutical preparations of Formulation Examples 1 to 3.

INDUSTRIAL APPLICABILITY

Owing to the present invention, it is possible to provide a crystal type of an isoxazole derivative having anti-inflammatory effect which makes it possible to carry out efficiently a process of formulation of the isoxazole derivative into a pharmaceutical preparation.

The invention claimed is:

1. A crystalline of 3-[(1S)-1-(2-fluorobiphenyl-4-yl)ethyl]-5-{[amino(morpholin-4-yl)methylene]amino}isoxazole that comprises the following angle of diffraction (2θ) and relative intensity in a powder X-ray diffraction pattern:

| 2θ (°) | Relative intensity (%) |
| --- | --- |
| 6.1 | 100 |
| 14.1 | 55 |
| 16.0 | 74 |
| 18.5 | 36 |
| 20.0 | 43 |
| 25.4 | 39. |

2. Crystalline 3-[(1S)-1-(2-fluorobiphenyl-4-yl)ethyl]-5-{[amino(morpholin-4-yl)methylene]amino}isoxazole according to claim 1, which is in a grounded state and has an undersize particle D50% particle size of 10 μm or less.

* * * * *